(12) United States Patent
Aronhalt et al.

(10) Patent No.: US 10,441,459 B2
(45) Date of Patent: Oct. 15, 2019

(54) METHODS AND DEVICES FOR ACTIVATING BROWN ADIPOSE TISSUE WITH COOLING

(75) Inventors: Taylor W. Aronhalt, Loveland, OH (US); Lee M. Kaplan, Wellesley, MA (US); Nicholas Stylopoulos, Boston, MA (US); Jason L. Harris, Hamilton, OH (US); Dwight Henninger, Waynesville, OH (US); James W. Voegele, Cincinnati, OH (US); Mark S. Ortiz, Milford, OH (US)

(73) Assignees: Ethicon Endo-Surgery, Inc., Cincinnati, OH (US); The General Hospital Corporation, Boston, MA (US)

(*) Notice: Subject to any disclaimer, the term of this patent is extended or adjusted under 35 U.S.C. 154(b) by 482 days.

(21) Appl. No.: 13/977,555

(22) PCT Filed: Dec. 21, 2011

(86) PCT No.: PCT/US2011/066415
§ 371 (c)(1),
(2), (4) Date: Dec. 12, 2014

(87) PCT Pub. No.: WO2013/115756
PCT Pub. Date: Aug. 8, 2013

(65) Prior Publication Data
US 2015/0119849 A1    Apr. 30, 2015

Related U.S. Application Data

(60) Provisional application No. 61/428,013, filed on Dec. 29, 2010.

(51) Int. Cl.
*A61F 7/10* (2006.01)
*A61F 7/02* (2006.01)
*A61F 7/00* (2006.01)

(52) U.S. Cl.
CPC .............. *A61F 7/10* (2013.01); *A61F 7/106* (2013.01); *A61F 2007/0035* (2013.01);
(Continued)

(58) Field of Classification Search
CPC ................................................ A61F 2007/0298
See application file for complete search history.

(56) References Cited

U.S. PATENT DOCUMENTS

| 5,540,730 A | 7/1996 | Terry, Jr. et al. |
| 6,645,229 B2 | 11/2003 | Matsumura et al. |

(Continued)

FOREIGN PATENT DOCUMENTS

| WO | 94/00086 A1 | 1/1994 |
| WO | 2012/092049 A2 | 7/2012 |

(Continued)

OTHER PUBLICATIONS

Namer—TRPA1 and TRPM8 activation in humans effects of cinnamaldedhyde and menthol. NeuroReport. 2005. 16(9) Jun. 21, 2005.*

(Continued)

*Primary Examiner* — Luther Behringer
(74) *Attorney, Agent, or Firm* — Mintz Levin Cohn Ferris Glovsky and Popeo, P.C.

(57) ABSTRACT

Methods and devices are provided for activating brown adipose tissue (BAT) with cooling. Generally, the methods and devices can activate BAT to increase thermogenesis, e.g., increase heat production in the patient, which over time can lead to weight loss and/or improved metabolic function. In one embodiment, a medical device is provided that activates BAT by cooling tissue having a high density of cold sensitive thermoreceptors and/or by cooling BAT depots directly, thereby increasing thermogenesis in the (Continued)

BAT and inducing weight loss and/or improved metabolic function through energy expenditure.

19 Claims, 4 Drawing Sheets

(52) U.S. Cl.
CPC ............... *A61F 2007/0036* (2013.01); *A61F 2007/0044* (2013.01); *A61F 2007/0047* (2013.01); *A61F 2007/029* (2013.01); *A61F 2007/108* (2013.01)

(56) References Cited

U.S. PATENT DOCUMENTS

| | | | |
|---|---|---|---|
| 7,264,602 | B1 | 9/2007 | Longsworth |
| 2005/0045498 | A1 | 3/2005 | Purcell et al. |
| 2007/0100387 | A1 | 5/2007 | Gerber |
| 2008/0183164 | A1* | 7/2008 | Elkins et al. ............... 606/21 |
| 2008/0262411 | A1* | 10/2008 | Dobak ............ A61K 31/135 604/20 |
| 2009/0082641 | A1 | 3/2009 | Giftakis et al. |
| 2009/0202387 | A1 | 8/2009 | Dlugos, Jr. et al. |
| 2010/0274332 | A1* | 10/2010 | Hirakawa ............ A47C 21/042 607/114 |
| 2010/0312295 | A1 | 12/2010 | Vase et al. |
| 2011/0190856 | A1* | 8/2011 | Burke .................... A41D 1/06 607/112 |
| 2011/0270360 | A1 | 11/2011 | Harris et al. |
| 2012/0290023 | A1 | 11/2012 | Boyden et al. |

FOREIGN PATENT DOCUMENTS

| | | |
|---|---|---|
| WO | 2012/092056 A1 | 7/2012 |
| WO | 2012/092057 A1 | 7/2012 |

OTHER PUBLICATIONS

Vorvick, LJ. "Body Temperature Norms." Mar. 9, 2017. Retrieved Mar. 28, 2017 from //medlineplus.gov/ency/article/001982.htm.*
Berg, A., Getting a grip on being cool on a hot day. New York Times. Dec. 13, 2005. 2 pages.
Ciabattoni, E., Just cool it. Stanford Magazine. Jul./Aug. 2005, 6 pages.
Grahn et al., Recovery from mild hypothermia can be accelerated by mechanically distending blood vessels in the hand. J Appl Physiol. 1998;85:1643-1648.
[No Author Listed] Cooling Techniques. Resuscitation Central. Retrieved from <http://www.resuscitationcentral.com/hypothermia/cooling-techniques>. 2010, 4 pages.
No Author Listed] Researchers Turn to Silver Nanoparticles to Reinvent Implantable-Device Batteries. Medtechinsider. Retrieved from <http://medtechinsider.com/archives/12240>. Feb. 11, 2010, 4 pages.
Bartelt et al., Brown adipose tissue activity controls triglyceride clearance. Nat Med. Feb. 2011;17(2):200-5.
Masamoto et al., Intragastric administration of TRPV1, TRPV3, TRPM8, and TRPA1 agonists modulates autonomic in thermoregulation different manners in mice. Biosci Biotechnol Biochem. May 2009;73(5):1021-7.
Rothwell et al., A role for brown adipose tissue in diet-induced thermogenesis. Nature. Sep. 6, 1979;281(5726):31-5.
Saito et al., High incidence of metabolically active brown adipose tissue in healthy adult humans: effects of cold exposure and adiposity. Diabetes. Jul. 2009;58(7):1526-31.
Stylopouloset al., Roux-en-Y gastric bypass enhances energy expenditure and extends lifespan in diet-induced obese rats. Obesity (Silver Spring). Oct. 2009;17(10):1839-4.
Van Marken Lichtenbelt et al., Cold-activated brown adipose tissue in healthy men. N Engl J Med. Apr. 9, 2009;360(15):1500-8.
Virtanen et al., Functional brown adipose tissue in healthy adults. N Engl J Med. Apr. 9, 2009;360(15):1518-25.
International Search Report and Written Opinion for Application No. PCT/US2011/66415 dated Jul. 19, 2013 (16 Pages).
Namer et al., TRPA1 and TRPM8 activation in humans: effects of cinnamaldedhyde and menthol. Neuroreport. Jun. 21, 2005;16(9):955-959. Abstract only. Retrieved from <http://journals.lww.com/neuroreport/Abstract/2005/06210/TRPA1_and_TRPM8_activation_in_humans_effects_of.15.aspx> on Jul. 4, 2013. 1 page.

* cited by examiner

METHODS AND DEVICES FOR ACTIVATING BROWN ADIPOSE TISSUE WITH COOLING

CROSS REFERENCE TO RELATED APPLICATIONS

The present application claims priority to International Application No. PCT/US11/66415 entitled "Methods And Devices For Activating Brown Adipose Tissue With Cooling" filed Dec. 21, 2011, and to U.S. Provisional Patent Application No. 61/428,013 entitled "Methods And Devices For Activating Brown Adipose Tissue" filed Dec. 29, 2010, which are hereby incorporated by reference herein in their entireties.

FIELD OF THE INVENTION

The present invention relates to methods and devices for inducing weight loss and/or improved metabolic function, and in particular to methods and devices for activating brown adipose tissue.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure and/or altering a patient's metabolism, e.g., a basal metabolic rate, leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity and in particular for activating BAT.

SUMMARY OF THE INVENTION

The present invention generally provides methods and devices for activating brown adipose tissue. In one embodiment, a medical method is provided and can include positioning a cooling device in contact with tissue of a patient in a selected region of the patient's body that has a high density of cold sensitive thermoreceptors. The method can also include activating the cooling device to lower a temperature of the tissue in the selected region by a predetermined amount and for a predetermined treatment period that is sufficient to activate brown adipose tissue and increase energy expenditure of the brown adipose tissue. In some embodiments, positioning a device in contact with tissue of a patient can include positioning the device proximate to at least one of a wrist, an ankle, a hand palm, and a foot sole. In addition, the brown adipose tissue can be at a supraclavicular region on one of a left and right side of a sagittal plane of the patient.

While the predetermined amount can be any suitable value, in some embodiments, it can be in the range of about 5 degrees Celsius to about 20 degrees Celsius, about 0.3 degrees Celsius to about 3 degrees Celsius, etc. In addition, the cooling device can apply a temperature to the tissue in a range of about 0.3 degrees Celsius below a normal body temperature to about 20 degrees Celsius below the normal body temperature and/or in a range of about 0.3 degree Celsius below ambient temperature to about 20 degrees Celsius below ambient temperature. The cooling device can optionally maintain a core temperature of a body 0.3 degrees Celsius below its normal temperature. The treatment period can be any suitable time effective to increase energy expenditure of BAT. For example, the predetermined treatment period can be in a range of about 5 minutes to about 4 hours. In addition, the predetermined treatment period can be in a range of about 15 minutes to about 1 hour and/or in a range of about 6 hours to about 12 hours.

In some embodiments, positioning the cooling device in contact with tissue of the patient can include transcutaneously applying the device to an exterior skin surface of the patient. In addition, positioning the cooling device in contact with tissue of the patient can include subcutaneously positioning at least a portion of the cooling device within the patient. Further, positioning the cooling device in contact with tissue of a patient can include implanting the cooling device entirely within the patient. In one embodiment, cooling can be continuously delivered to, and/or thermal energy can be continually removed from, the patient for a predetermined amount of time. In other embodiments, the cooling device can be in continuous contact with the tissue, but cooling can be delivered intermittently.

The cooling device can be applied to the tissue of the patient for a predetermined therapy duration. While the predetermined therapy duration can be for any amount of time, in an exemplary embodiment, it can be for at least four weeks. In other embodiments, it can be in a range of about 2 days to about 4 weeks. During the predetermined therapy duration, the cooling device can repeatedly be applied to and removed from the tissue. By way of non-limiting example, during the predetermined therapy duration, the cooling device can be applied to the tissue for 12 hours and then removed from the tissue for 12 hours. Alternatively, the cooling device can be applied and/or worn continuously during the therapy duration while being engaged in active cooling for intermittent treatment periods during the therapy duration. The cooling device can include one of an endothermic gel pack patch, a Peltier device, a cooling floor mat, a cooling bandage, a cooling bracelet, and a cooling vest. Further, the cooling device can include a fluid reservoir to effect evaporative cooling. The cooling device can also effect cooling through one of inductive coupling, refrigeration, passive cooling, evaporation, topical cooling, heat exchange, and thermal transfer.

In one embodiment, the cooling device can include an infusion pump for delivery of at least one agonist to at least one thermal TRP channel. The thermal TRP channel can be one of TRPV1, TRPM8, and TRPA1, and the agonist can be one of capsaicin, resiniferatoxin, menthol, 1,8-cineole, cinnamaldehyde, and allyl isothiocyanate.

An exemplary method can also include removing the cooling device from the patient, repositioning the cooling device in contact with tissue of the patient in another region of the patient's body that has a high density of cold sensitive thermoreceptors, and activating the cooling device to a temperature lower than that of the tissue in the other region by a predetermined amount and for a predetermined treatment period that is sufficient to activate brown adipose tissue and increase energy expenditure of the brown adipose tissue. The cooling device can be activated in response to a trigger event including at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device.

In some embodiments, a cooling device can include a cooling housing configured to remove thermal energy from tissue and a controller configured to turn the cooling housing on, turn the cooling housing off, or both. The controller can be configured to be located remotely from the patient and to be in electronic communication with the cooling housing. In some embodiments, the controller can be configured to be implanted entirely within the patient.

In another aspect, a medical method is provided and can include delivering an agonist to a thermal TRP channel of the body to activate brown adipose tissue and increase energy expenditure of the brown adipose tissue. The agonist can be one of capsaicin, resiniferatoxin, menthol, 1,8-cineole, cinnamaldehyde, and allyl isothiocyanate. The thermal TRP channel can be one of TRPV1, TRPM8, and TRPA1. In some embodiments, delivering an agonist can include administering a pill configured to dissolve over a predetermined time at a predetermined location within a body. The predetermined time can be, for example, about 5 minutes, and the predetermined location can be an intragastric space. In one embodiment, delivering an agonist can include injecting the agonist directly into an intragastric space. In addition, delivering an agonist can include implanting an infusion apparatus within an intragastric space to deliver the agonist over a predetermined amount of time.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
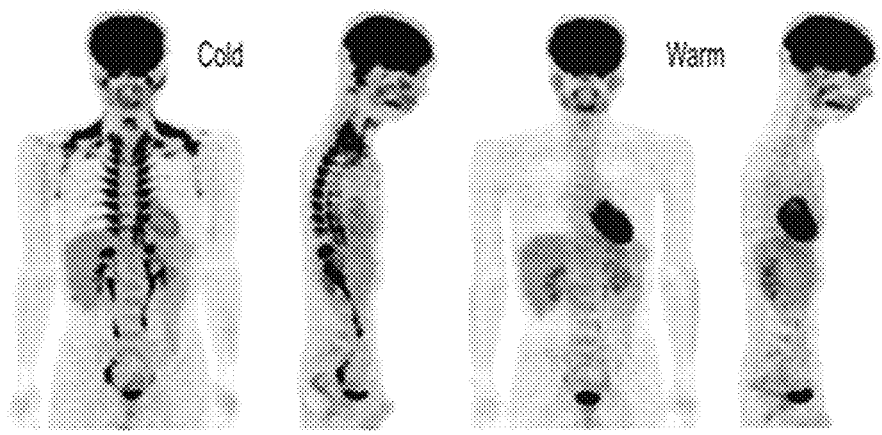
FIG. 1 is a schematic view of PET-CT images showing the locations of BAT depots in a patient subject to a cold environment and in the patient in a normal, warm environment.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for activating brown adipose tissue (BAT). In general, the methods and devices can activate BAT to increase thermogenesis, e.g., increase heat production and energy expenditure in the patient, which can treat metabolic disorders, such as obesity, diabetes, and hyperlipidemia. Therefore, activating BAT to increase thermogenesis can, over time, lead to one or more of weight loss, a change in the metabolism of the patient, e.g., increasing the patient's basal metabolic rate, and improvement of comorbidities in obese or non-obese patients, e.g., Type II diabetes, high blood pressure, etc. In an exemplary embodiment, a medical device is provided that activates BAT by cooling a selected area and/or areas of a body having cold sensitive thermoreceptors to activate the BAT, thereby increasing thermogenesis in the BAT and inducing weight loss and/or improving metabolic function through energy expenditure. As will be appreciated by a person skilled in the art, an obese patient can have a body mass index (BMI) greater than 30 $kg/m^2$, and a non-obese patient can have a BMI less than 30 $kg/m^2$. In this way, weight loss and/or improved metabolic function can be induced without performing a major surgical procedure, without relying on administration of one or more pharmaceuticals, and without surgically altering a patient's stomach and/or other digestive organs.

Following a surgical procedure to treat obesity such as Roux-en-Y gastric bypass (RYGB), a patient can lose weight due to an increase in energy expenditure, as demonstrated in a rodent model for example in Stylopoulos et al., "Roux-en-Y Gastric Bypass Enhances Energy Expenditure And Extends Lifespan In Diet-Induced Obese Rats," Obesity 17 (1 Oct. 2009), 1839-47. Unpublished data from Stylopoulos et al. show that RYGB is also associated with increased levels of uncoupling protein 1 (UCP1), which is an uncoupling protein in mitochondria of BAT, as well as with a significant reduction in the size of fat stores within BAT and an increased volume of BAT. It thus appears that RYGB causes activation of BAT, although as discussed above, surgical procedures to treat obesity, such as gastric bypass, risk if not necessarily cause a variety of undesirable results. Devices and methods to activate BAT without a major surgical procedure like RYGB, but instead with cooling areas of the body having cold sensitive thermoreceptors to increase energy expenditure are therefore provided.

One characteristic of BAT that distinguishes it from white adipose tissue (WAT) stores is the high number of mitochondria in a single BAT cell. This characteristic makes BAT an excellent resource for burning energy. Another distinguishing characteristic of BAT is that when activated, UCP1 is utilized to introduce inefficiency into the process of adenosine triphosphate (ATP) creation that results in heat generation. Upregulation of UCP1 is therefore a marker of BAT activation. Furthermore, the controlled activation of BAT can be optimized, leading to weight loss and/or improved metabolic function, by reducing the stores of triglycerides in WAT. A person skilled in the art will appreciate that exposure to cold temperature leads to the activation of BAT to help regulate body temperature. This knowledge allows the location of BAT to be readily assessed using positron emission tomography—computed tomography (PET-CT) imaging. FIG. 1 shows scans of a patient subjected to a cold environment (left two images) and the same patient scanned in a normal, warm environment (right two images). Shown in black are regions of intense glucose uptake—namely, the brain, the heart, the bladder, and in the cold environment, BAT. However these images show the locations of BAT depots—namely the nape of the neck, the supraclavicular region, over the scapula, alongside the spinal cord, and around the kidneys as referenced by, for example, Rothwell et al, "A Role For Brown Adipose Tissue In Diet-Induced Thermogenesis," Nature, Vol. 281, 6 Sep. 1979, Virtanen et al., "Functional Brown Adipose Tissue in Healthy Adults," The New England Journal of Medicine, Vol. 360, No. 15, Apr. 9, 2009, 1518-1525, and van Marken Lichtenbelt et al., "Cold-Activated Brown Adipose Tissue in Healthy Men," The New England Journal of Medicine, Vol. 360, No. 15, Apr. 9, 2009, 1500-1508. Applying cold to BAT and/or otherwise activating BAT as discussed herein can thus improve glucose tolerance in a patient, and thereby be effective to treat a metabolic disease such as diabetes independent of weight loss and regardless of whether the patient is obese or non-obese. For example, in their paper, Bartelt et al., "Brown adipose tissue activity controls triglyceride clearance," Nature Medicine, Vol. 17, February 2011, 200-205, describe exposing mice to cold and detecting improved glucose tolerance after exposure to cold.

In some embodiments, cooling of tissue that has and/or is proximate to tissue having a high density of cold sensitive thermoreceptors to activate BAT can be combined with one or more treatments, before and/or after cooling, which can help encourage BAT stimulation and/or increase an amount of BAT in a patient. For non-limiting example, a pharmaceutical can be administered to a patient, the patient can be electrically stimulated, the patient can be heated, a BAT-stimulation procedure can be performed on the patient directed to a BAT depot and/or to a nerve innervating BAT, the patient can engage in weight loss therapies, and/or a surgical procedure can be performed on the patient, such as a procedure to induce weight loss and/or to improve metabolic function, e.g., glucose homeostatic, lipid metabolism, immune function, inflammation/anti-inflammatory balance, etc. Providing electrical stimulation, e.g., using an implanted electrical stimulation device, such that the BAT depot can be simultaneously activated through a mechanism associated with a lowered body temperature and electrically stimulated, thereby potentially further encouraging additive or synergistic activation of the BAT. Non-limiting examples of a nerve stimulation technique configured to stimulate a nerve innervating BAT include delivery of a medium to the nerve that induces an action potential in the nerve, e.g., electricity, light, mechanical manipulation or vibration, a magnetic field, a chemical substance, etc. Exemplary embodiments of methods and devices for delivering an electrical signal to activate BAT are described in more detail in U.S. Pat. Pub. No. 2011/0270360 filed Dec. 29, 2010 entitled "Methods And Devices For Activating Brown Adipose Tissue Using Electrical Energy." Non-limiting examples of a BAT-stimulation procedure include inducing differentiation of muscle, WAT, preadipocytes, or other cells to BAT, and/or implanting or transplanting BAT cells into a patient. Non-limiting examples of implanting or transplanting BAT cells include removing cells from a patient, culturing the removed cells, and reimplanting the cultured cells; transplanting cells from another patient; implanting cells grown from embryonic stem cells, adult stem cells, or other sources; and genetically, pharmacologically, or physically altering cells to improve cell function. Non-limiting examples of such weight loss therapies include a prescribed diet and prescribed exercise. Non-limiting examples of such a surgical procedure include gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, vagal nerve stimulation, duodenal endoluminal barrier, and procedures that allow for removal of food from the stomach. Combining one or more treatments, particularly a weight loss therapy or a weight loss surgical procedure which does not activate BAT, e.g., a procedure other than RYGB, biliopancreatic diversion (BPD) with or without duodenal switch, or some duodenal or other intestinal barrier (e.g., a prescribed diet and/or exercise program, adjustable gastric banding, vertical banded gastroplasty, sleeve gastrectomy, gastric plication, Magenstrasse and Mill, intragastric balloon therapy, some duodenal or other intestinal barrier, and small bowel transposition, with a means for acute or chronic activation of BAT such as the cooling therapies discussed herein, can result in desirable patient outcomes through a combined approach.

Because BAT activation may lead to an increase in body temperature locally, regionally, or systemically, cooling of tissue to activate BAT can be combined with one or more heat dissipation treatments, before and/or after cooling of tissue. Non-limiting examples of such a heat dissipation treatment include inducing cutaneous/peripheral vasodilation, e.g., local or systemic administration of Alpha antagonists or blockers. In addition, protection of thermally affected tissue sites can be accomplished through the rotation of treatment between sites and/or the cycling of treatments at a given site with a sufficient interval between cycles for the tissue to return to a target temperature. Furthermore, tachyphylaxis can be avoided by varying the anatomical location to which cooling is administered, e.g., by moving cooling between a patient's left wrist and right wrist.

Figure 2:
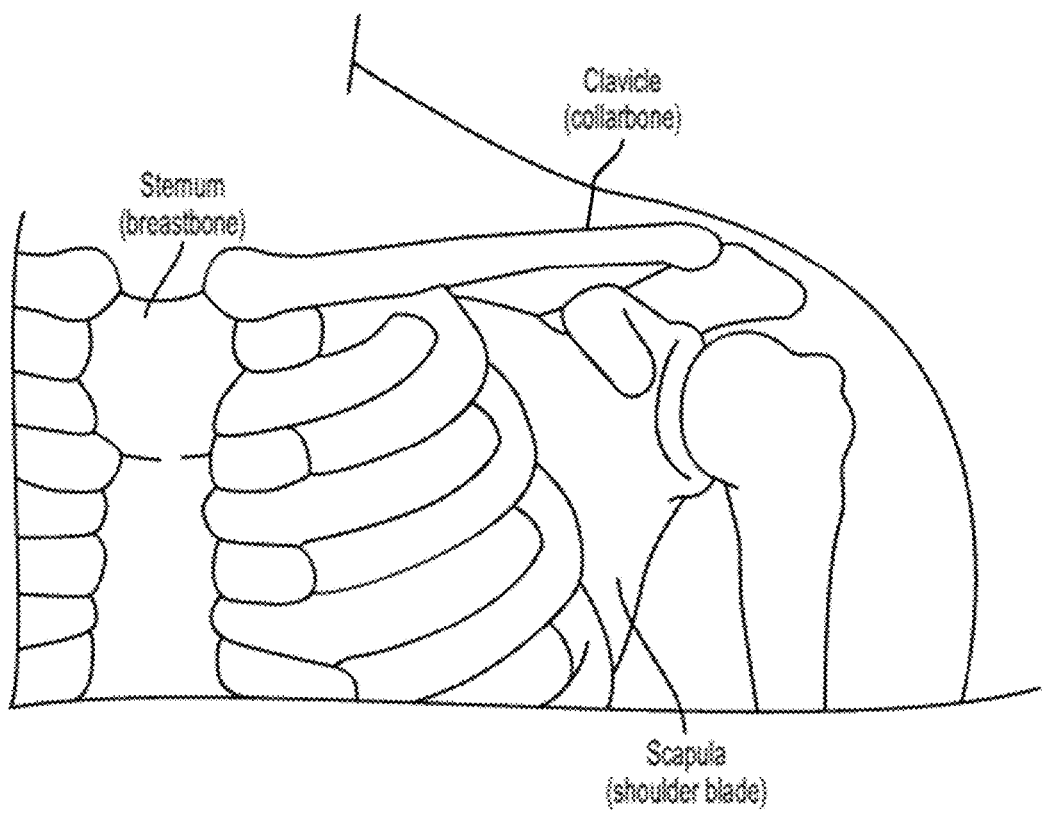
FIG. 2 is a transparent view of a portion of a human neck, chest, and shoulder area with a shaded supraclavicular region.

Target areas for cooling can include a patient's wrists, palms of the hands, ankles, soles of the feet, gut, airway, and urinary tract, as well as areas proximate to BAT depots, e.g., a supraclavicular region, the nape of the neck, over the scapula, alongside the spinal cord, near proximal branches of the sympathetic nervous system that terminate in BAT depots, and around at least one of the kidneys. Any BAT depot can be selected for activation. For non-limiting example, in one embodiment illustrated in FIG. 2 a BAT depot can be activated in an area over a scapula in a supraclavicular region S. Identification of one or more BAT depots for activation can be determined on an individualized patient basis by locating BAT depots in a patient by scanning the patient using PET-CT imaging, tomography, thermography, or any other technique, as will be appreciated by a person skilled in the art. It is further conceived that non-radioactive based imaging techniques could be used to measure changes in blood flow associated with the activation of BAT within a depot. The first technique involves the use of a contrast media containing microbubbles. The contrast media is injected into a patient whose BAT has been activated. An energy sources such as low frequency ultrasound can be applied to the region of interest to cause destruction of these bubbles. The rate of refill of this space is quantified. Increased rates of refill can be associated with active BAT depots. Another technique involves the use of a contrast media containing a fluorescent media. The contrast media can be injected into a patient whose BAT has been activated. A needle based probe can be placed in the region of interest that is capable of counting the amount of fluorescent contrast that passes the probe. Increased counts per unit time corresponds to increased blood flow and can be associated with activated BAT depots. In the course of treating a patient, one or more areas having cold sensitive thermoreceptors can be stimulated to activate any one or more BAT depots and can be stimulated simultaneously, e.g., such that two or more BAT depots are concurrently stimulated, or stimulated sequentially, e.g., different BAT depots being stimulated at different times.

Methods of measuring BAT activation can be determined through energy expenditure involving continuous measurements of heat output (direct calorimetry) or inhaled/exhaled gas exchange (indirect calorimetry) in subjects. The term "energy expenditure," as used herein, refers to the amount of energy (calories), that a person uses to breathe, circulate blood, digest food, support routine physiological functions and be physically active. To prevent weight gain, energy intake (caloric intake) must be balanced with energy expenditure.

Measurements of the heat released from a person's body can determine how much energy an activity has consumed. In addition, indirect calorimetry can measure oxygen consumption, carbon dioxide production and/or nitrogen excretion to calculate a ratio that reflects energy expenditure. A component of energy expenditure can be calculated as basal energy expenditure, which is the amount of energy required to maintain the body's normal metabolic activity, i.e. respiration, body temperature, etc.

Such energy expenditure or metabolic heat production in a subject can be assessed using several techniques. For measurement of the basal metabolic rate, the subject must be within its thermal neutral zone, which is the range of environmental temperatures across which the subject's body temperature can be maintained at its basal metabolic rate. The subject must be in a postabsorptive state, quiescent, in sexual repose, and resting but conscious. Since the latter prerequisite is often difficult to achieve with non-human subjects, the fasting heat production is used for animals which are quiet, but not necessarily resting.

Energy expenditure or metabolic heat production can be detected externally by a subject's heat loss pattern. Radiation, through which 40 to 60% of heat is lost from a subject, can be readily measured using any commercially available pyrometer or temperature sensor, since most radiated heat loss can be displayed in the 5-12 μm wavelength range of the electromagnetic spectrum. Direct and indirect calorimetry are further methods for assessing energy expenditure. Direct calorimetry measures heat loss from a subject directly by placing the subject at rest or exercising in a chamber surrounded by a waterjacket. Heat emitted from the subject raises the temperature of the water. The difference in the temperature of water entering and leaving the chamber reflects the subject's energy expenditure. Indirect calorimetry measures gas exchange and relates it to heat production. Indirect calorimetry involves monitoring of the amount of oxygen consumed (or conversely, the amount of carbon dioxide produced), and calculating the amount of energy expended by the subject, depending on the food substrate being utilized (e.g., fat, carbohydrate or protein).

Metabolic rate can also be measured through the use of doubly labeled water methods in which the average metabolic rate of an organism is measured over time. The use of doubly labeled water methods measures the subject's carbon dioxide production. Oxygen in body water can be lost in carbon dioxide, excretions and evaporative losses. However, hydrogen can only be lost through body water loss. Taking advantage of the change in body water and carbon dioxide production over time can be used to mathematically calculate metabolic rate.

Selective cooling of tissue by an exemplary cooling device can be achieved through continuous and/or periodic application of the device to tissue for various treatment periods. The treatment periods can continue for a therapy duration, e.g., for a time sufficient to accomplish an increase in energy expenditure of BAT. An exemplary treatment period can range in time from a few seconds to 24 hours or more. For example, in the case of continuous cooling, the cooling device can be applied to tissue for a treatment period in the range of about 1 second to about 1 hour, about 4 hours, about 8 hours, about 12 hours, and/or about 24 hours; about 30 minutes to about 1 hour, about 4 hours, about 8 hours, and/or about 12 hours; about 1 hour to about 2 hours, about 4 hours, and/or about 6 hours; about 2 hours to about 3 hours and/or about 4 hours, etc. In the case of periodic cooling, a cooling device can remain in contact with tissue for the entire treatment period, but cooling can be applied to tissue for an amount of time and then removed from tissue for an amount of time. The amount of time that cooling is applied and/or not applied can be any fraction of the times indicated above for a treatment period and/or can be the entirety of any of the times indicated above. The therapy duration can be in the range of about 24 hours to about 4 weeks or more, for example, 36 hours, 48 hours, 1 week, 2 weeks, 3 weeks, 4 weeks, 5 weeks, 6 weeks, 2 months, 6 months, and/or a year. In some embodiments, a treatment period and/or a therapy duration for cooling can be coordinated with an event in a patient's life to enhance the treatment and/or to provide another beneficial effect. Such an event can include eating, sleeping, circadian rhythms, low energy expenditure states, menstrual cycles in women, medication intake (e.g., an appetite suppressant such as topiramate, fenfluramine, etc.), a nutrient change in the patient (e.g., a change in glucose or glucose transporters, amino acids, bile acids, free fatty acids and fatty acid transporters, and their metabolites, etc.), and a manually-generated or automatically-generated signal from a controller in electronic communication, wired and/or wireless, with the device. Non-limiting examples of nutrients include lipids such as bile acids, cholesterol and its metabolites, aliphatic fatty acids, peptides and proteins, etc. The controller can be internal to the device, be located external from but locally to device, or be located external and remotely from device. As will be appreciated by a person skilled in the art, the controller can be coupled to the device in any way, e.g., hard-wired thereto, in wireless electronic communication therewith, etc. In some embodiments, multiple devices can be applied to a patient, and at least two of those devices can be configured to deliver a chemical based on different individual trigger events or combinations of trigger events.

In general, BAT is activated when a subject is in a cold environment for a sufficient amount of time. In addition, colder temperatures generally lead to shorter time periods. There are a variety of temperatures that can lead to BAT activation. For example, suitable temperatures can be in a range of about 4° C. to about 16° C., from about 6° C. to about 14° C. In their paper, van Marken Lichtenbelt et al. describe a method for activating BAT wherein patients were subjected to mild cold (16° C.) for 2 hours in a controlled environment. Similarly, M. Saito et al., "High Incidence of Metabolically Active Brown Adipose Tissue in Healthy Adult Humans: Effects of Cold Exposure and Adiposity," Diabetes, Vol. 58, July 2009, 1526-1531. subjected patients to mild cold (19° C.) for 2 hours in a controlled environment and observed activated BAT in some, but fewer patients than in van Marken Lichtenbelt et al. Subjecting a patient to cold a cold environment is effective, but not practical to achieve chronic activation of BAT. In some embodiments, a patient's entire body can be cooled. In other embodiments, cooling can be directly applied to tissue at certain areas of the body with a high density of cold sensitive thermoreceptors, such as the wrists, ankles, palms of the hands, soles of the feet, etc. as indicated above. In still other embodiments, cooling can be applied near and/or directly to BAT depots.

Figure 3:
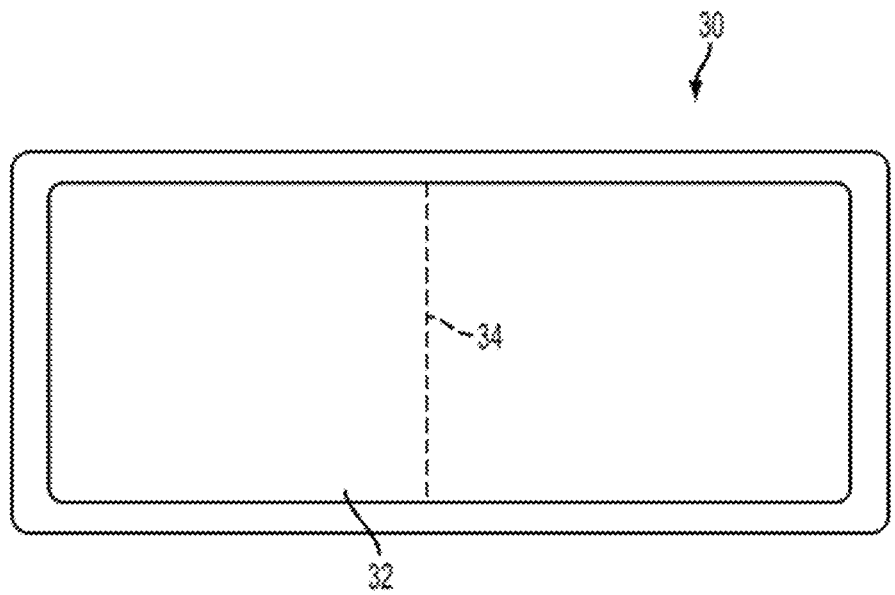
FIG. 3 is a top view of an exemplary cooling device in the form of an endothermal cold pack.

Any device capable of cooling a body and/or an area of the body can be used to accomplish BAT activation. For example, as shown in FIG. 3, a cold pack 30 is provided for applying to tissue. While any cold pack known in the art can be used, in the illustrated embodiment, the cold pack 30 can have an enclosure 32 with a powdered solute and a liquid sealed inside the enclosure 32. The powdered solute and the liquid can be segregated within the enclosure 32 by a membrane 34. Rupturing the membrane 34 can be effective to mix the liquid and the powdered solute to produce an endothermic solution within the enclosure 32. Substantially all of the solute can rapidly dissolve within the liquid such that the cold pack 30 quickly reaches its cooling temperature. In another embodiment, the cold pack 30 can include an absorbent core within the enclosure 32. The absorbent core can retain the endothermic solution such that the absorbent core spreads the endothermic solution throughout the enclosure 32. Spreading the endothermic solution throughout the enclosure 32 can produce a uniform cooling temperature throughout the cold pack 30. The cold pack 30 can then be applied to tissue at an area of a patient's body with a high density of cold sensitive thermoreceptors and/or to an area proximate a BAT depot.

Figure 4:
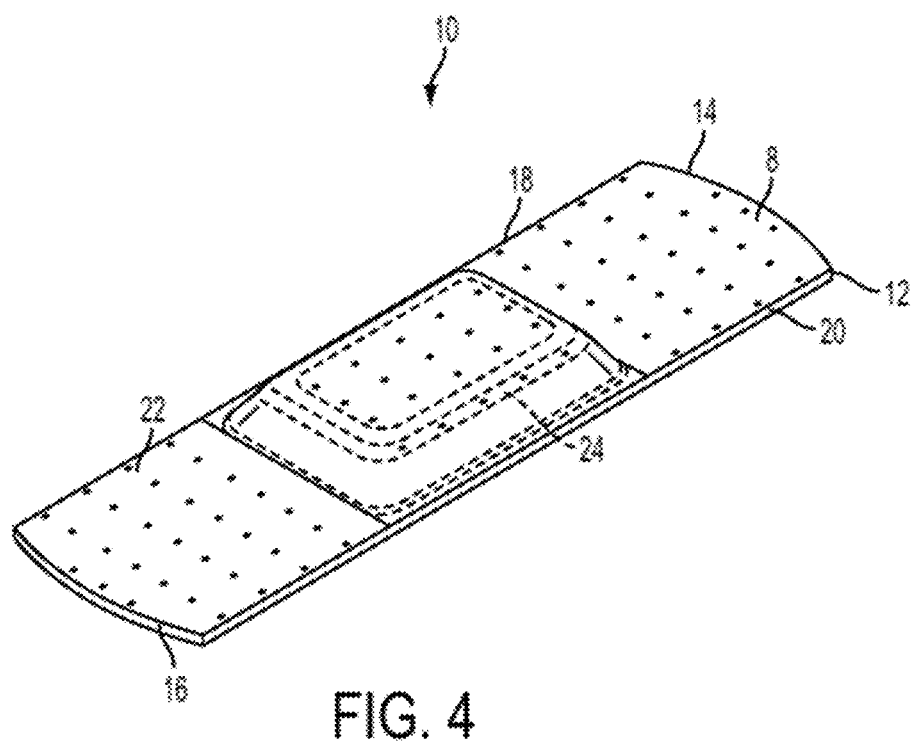
FIG. 4 is a perspective view of an exemplary cooling device in the form of an adhesive gel pack.

In another embodiment, illustrated in FIG. 4, a bandage assembly 10 is provided that can include a panel 8 that is substantially flexible. The panel 8 can include a first end edge 14, a second end edge 16, a first lateral edge 18, and a second lateral edge 20. The panel 8 can have a first side 22 and second side 12. An adhesive can be attached to and can cover the second side 12 of the panel 8. A housing 24 having a gel therein can be attached to the first side 22 of the panel 8. The housing 24 can be positioned between the first and second end edges 14, 16, and the gel can be selectively cooled. The panel 8 can be attached to an area of tissue having a high density of cold sensitive thermoreceptors and/or to an area proximate a BAT depot to provide cooling to the area.

Figure 4A:
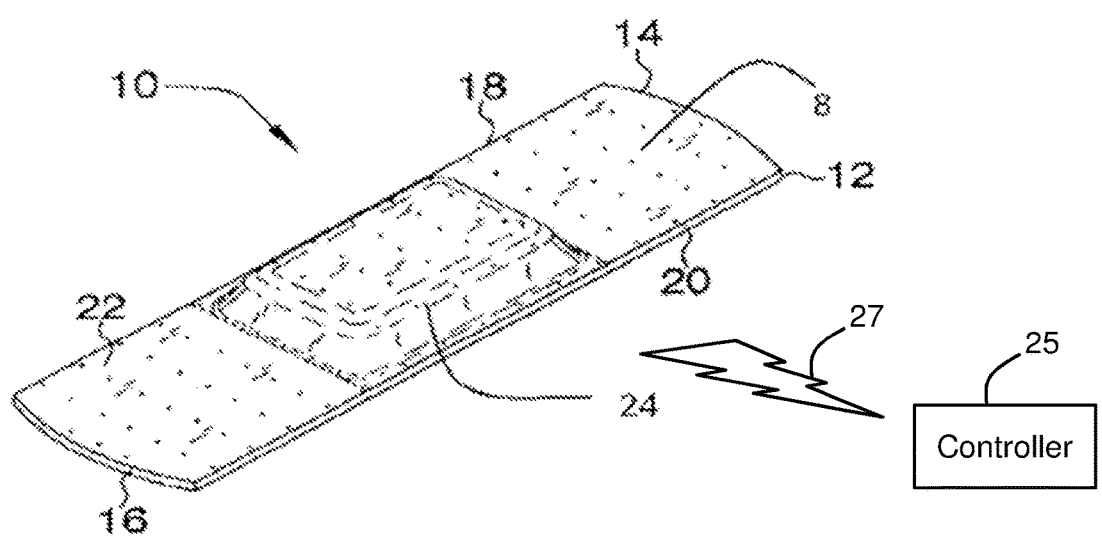
FIG. 4A is a perspective view of the cooling device of FIG. 4 showing a controller thereof.
Figure 5:
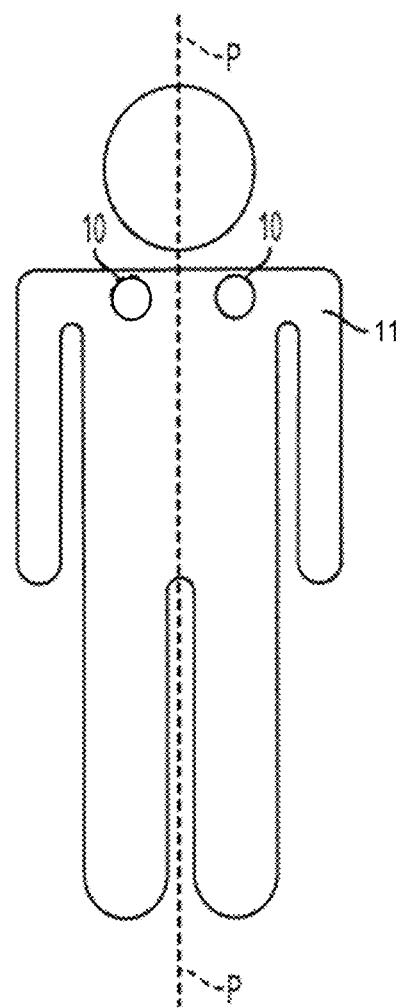
FIG. 5 is a front view of a body showing one embodiment of a cooling device positioned on opposite sides of the body's sagittal plane.

As shown in FIG. 4A, a controller 25 is configured to turn the cooling housing 24 on, turn the cooling housing 24 off, or both. The controller 25 can be configured to be located remotely from the patient and to be in electronic communication 27 with the cooling housing 24, as shown in FIG. 4A. In some embodiments, the controller 25 can be configured to be implanted entirely within the patient. The housing 24 can include circuitry configured to interact with the controller 25 such that the controller can control at least some functions of the cooling device as discussed herein.

A person skilled in the art will appreciate the many various cooling devices that can be utilized to apply cooling to tissue. In some embodiments, a cooling floor pad can be utilized to effect cooling the soles of a patient's feet. The pad can be placed next to a chair and/or under a desk and can provide periodic cooling as necessary. For example, a patient can put one foot on the pad and then switch to the other foot to effect activation of BAT. The pad may be a Thermoelectric cooler using the Peltier effect to create a heat flux between the junction of two different types of materials. A Peltier cooler or thermoelectric heat pump is a solid-state active heat pump which transfers heat from one side of the device to the other side against the temperature gradient (from cold to hot), with consumption of electrical energy. Such an instrument is also called a Peltier device, solid state refrigerator, or thermoelectric cooler (TEC). Many alternatives could serve this same purpose—such as rankine cycle cooler with the cooling coils conductively connected to the cooling pad. In other embodiments, cooling can be provided by an article of clothing worn by a patient. For example, a patient can wear a cooling vest, bracelet, and/or anklet that can effect continuous and/or periodic cooling as desired. In one particular embodiment, a patient can wear a cooling vest, for example a vest configured to treat hypothermia, to sleep at night. The cooling vest can be configured to lower the core body temperature of the patient by about 0.3° C. below its normal range, thereby activating BAT.

In other embodiments, a cooling device can contain a reservoir or pad containing a fluid, such as water or alcohol, which can be effective to lower a surface temperature of tissue through evaporative cooling. In addition, non-limiting examples of other possible types of cooling can include inductive coupling; refrigeration; passive cooling; topical cooling using ointments, gels, etc.; heat exchange; and thermal transfer through conduction, convection, and/or radiation. With regard to heat exchange, a patient can wear a thermally conductive thread material having a high surface area to volume ratio to effectively dissipate heat to the surrounding environment, thus reducing body temperature. In addition, by pumping a fluid such as water, alcohol, and/or Freon™ through the heat exchanger material, a patient's internal body temperature can be reduced even more efficiently. Additionally, patient tissue contact with the thermally conductive material can be further enhanced by first applying a biocompatible thermally conductive compound to the skin prior to applying the conductive material to ensure the greatest heat transfer to the fibers.

Thermosensitive transient receptor potential channels (thermo TRP channels) can play a major role in controlling autonomic thermoregulation of the body. In some embodiments, agonists, such as capsaicin, resiniferatoxin, menthol, 1,8-cineole, cinnamaldehyde, and/or allyl isothiocyanate, can be injected to thermo TRP channels TRPV1, TRPM8 and TRPA1 to increase energy expenditure of BAT. There are a number of ways that an agonist can be introduced into a thermo TRP channel. In some embodiments, an agonist can be injected directly to a patient's intragastric space, such as into a patient's stomach. In other embodiments, a pill can be formulated with one or more combinations of the above-noted agonists. The pill can dissolve over a period of time, for example about 5 minutes, within the stomach such that the agonists are released to be absorbed into the thermo TRP channels. There are many other ways in which an agonist can be introduced. Non-limiting examples include an infusion pump, an implantable infusion apparatus, an insulin infusion pump, a pill/pill catcher system, intestinal brake inducing intraluminal therapeutic substance dosing devices and methods, intestinal brake systems and methods, and intraperitoneal delivery, among others.

Thermo TRP channels are also prevalent in the skin, making them especially available for activation by agonists such as capsaicin, resiniferatoxin, menthol, 1,8-cineole, cinnamaldehyde, and/or allyl isothiocyanate. These agonists can be imbedded in a topical cream, gel, or other delivery means to be administered by the patient or by a device to the region of the skin of interest.

For example, in one embodiment, an infusion style pump can be worn by a patient for the administration of agonists. In a surgical procedure, an anterior surface of the stomach can be brought into contact within the abdominal wall and fixed in place using fastener mechanisms known in the art. This configuration can create a pathway for the administration of agonists such as capsaicin, resiniferatoxin, menthol, 1,8-cineole, cinnamaldehyde, and/or allyl isothiocyanate into the intragastric space. A flexible catheter, for example, can connect the infusion pump to the intragastric space. The pump can deliver the agonists according to a prescribed algorithm to increase energy expenditure. This therapy can be combined with the use of a duodenal barrier, which can also be capable of increasing energy expenditure, to seek synergistic effects.

In use, some exemplary cooling devices can be in communication with a signal generator and/or control system. As will be appreciated by a person skilled in the art, a signal generator and/or control system can have a variety of sizes, shapes, and configurations, and can be external to the patient or implanted therein similar to a cardiac pacemaker. The signal generator or control system can communicate and/or control the cooling device to regulate the temperature of the cooling, the timing of each treatment period and/or therapy duration, as well as record data regarding a patient's statistics. Furthermore, the signal generator and/or control system can regulate the device periodically and/or continuously once activated, e.g., manually, automatically, etc. and can communicate with external cooling devices as well as cooling devices implanted within a patient.

An external signal generator or control system can be positioned near the patient's skin, e.g., using a belt, a necklace, a shirt or other clothing item, furniture or furnishings such as a chair or a pillow, or can be a distance away from the patient's skin, such as a source located elsewhere in the same room or the same building as the patient. If implanted, the signal generator or control system can include an internal power source, e.g., a battery, a capacitor, stimulating electrodes, a kinetic energy source such as magnets positioned within wired coils configured to generate an electrical signal within the coils when shaken or otherwise moved, etc. In one embodiment, a battery can include a flexible battery, such as a Flexion™ battery available from Solicore, Inc. of Lakeland, Fla. In another embodiment, a battery can include an injectable nanomaterial battery. The power source can be configured to be recharged by transcutaneous means, e.g., through transcutaneous energy transfer (TET) or inductive coupling coil, and/or can be configured to provide power for an extended period of time, e.g., months or years, regardless of how long the power source is intended to provide power to the device. In some embodiments, a power source can be configured to provide power for less than an extended period of time, e.g., about 7 days, such as if a battery is replaceable or rechargeable and/or if device real estate can be conserved using a smaller, lower power battery. In some embodiments, the signal generator can include an electrode patch onboard configured to generate a pulse, thereby eliminating a need for a battery.

The signal generator, control system, and/or any other portion of the external cooling device or implanted cooling device, as will be appreciated by a person skilled in the art, can be configured to measure and record one or more physical signals relating to the activation of BAT. For non-limiting example, the physical signals can include voltage, current, impedance, temperature, time, moisture, salinity, pH, concentration of hormones or other chemicals, etc. The recorded physical signals can be presented to the patient's physician for evaluation of system performance and efficacy of brown adipose activation. Also, the recorded physical signals can be used in a closed-loop feedback configuration to allow the device, e.g., the controller, to dynamically adjust the electrical signal settings used for treatment.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Patent Publication No. 2009/0202387 filed Feb. 8, 2008 and entitled "System And Method Of Sterilizing An Implantable Medical Device."

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical method, comprising:
positioning a cooling device in contact with tissue of a patient in a selected region of the patient's body that has a high density of cold sensitive thermoreceptors, wherein the cooling device includes a cold pack or a bandage assembly; and
activating the cooling device to lower a temperature of the tissue in the selected region by a predetermined amount and for a predetermined treatment period that is sufficient to activate brown adipose tissue and increase energy expenditure of the brown adipose tissue, wherein the cooling device is activated in response to a trigger event including at least one of a change in the patient's tissue impedance and the patient falling asleep.

2. The method of claim 1, wherein positioning the cooling device in contact with tissue of the patient comprises positioning the device proximate to at least one of a wrist, an ankle, a hand palm, and a foot sole.

3. The method of claim 1, wherein the brown adipose tissue is at a supraclavicular region on one of a left and right side of a sagittal plane of the patient.

4. The method of claim 1, wherein positioning the cooling device in contact with tissue of the patient comprises transcutaneously applying the device to an exterior skin surface of the patient.

5. The method of claim 1, wherein the cooling is continuously delivered to the patient throughout the predetermined treatment period.

6. The method of claim 1, wherein the cooling device is configured to effect evaporative cooling.

7. The method of claim 1, wherein the cooling device effects cooling through one of inductive coupling, refrigeration, passive cooling, evaporation, topical cooling, heat exchange, and thermal transfer.

8. The method of claim 1, further comprising delivering at least one agonist to at least one thermal TRP channel using the cooling device.

9. The method of claim 8, wherein the at least one thermal TRP channel is one of TRPV1, TRPM8, and TRPA1.

10. The method of claim 1, further comprising
removing the cooling device from the patient;
repositioning the cooling device in contact with tissue of the patient in another region of the patient's body that has a high density of cold sensitive thermoreceptors; and
activating the cooling device to lower a temperature of the tissue in the another region a predetermined amount and for a predetermined treatment period that is sufficient to activate brown adipose tissue and increase energy expenditure of the brown adipose tissue.

11. The method of claim 1, wherein the cooling device includes the bandage assembly, and the method further comprises removing thermal energy from the tissue using a cooling housing of the bandage assembly, and selectively turning the cooling housing on and turning the cooling housing off.

12. The method of claim 11, wherein the selective turning on and off is performed remotely from the patient.

13. The method of claim 1, wherein the predetermined treatment period is in a range of about 4 hours to about 12 hours.

14. The method of claim 1, wherein the cooling device delivers cold at a temperature in a range of about 4° C. to about 16° C.

15. The method of claim 1, further comprising:
positioning a second cooling device in contact with a second tissue of the patient in a second selected region of the patient's body that has a high density of cold sensitive thermoreceptors, wherein the second coolies device includes a cold pack or a bandage assembly; and
activating the second cooling device to lower a temperature of the second tissue in the second selected region to activate a second brown adipose tissue and increase energy expenditure of the second brown adipose tissue, wherein the second cooling device is activated in response to a second trigger event that is different from the trigger event, and the second trigger event includes a different one of the change in the patient's tissue impedance and the patient falling asleep.

16. The method of claim 1, wherein the cooling device includes the bandage assembly, and a controller causes the activation of the bandage assembly in response to a detection of the trigger event.

17. The method of claim 1, wherein the activation is causing the cooling device to start delivering cold to the patient.

18. The method of claim 1, wherein the trigger event also includes at least one of the patient eating, the patient resting, a threshold temperature of the patient, a directional orientation of the patient, and a blood chemistry change in the patient.

19. The method of claim 1, wherein the cooling device includes the cold pack.

* * * * *